United States Patent [19]

Rasmussen

[11] Patent Number: 5,324,304
[45] Date of Patent: Jun. 28, 1994

[54] INTRODUCTION CATHETER SET FOR A COLLAPSIBLE SELF-EXPANDABLE IMPLANT

[75] Inventor: Erik E. Rasmussen, Søbørg, Denmark

[73] Assignee: William Cook Europe A/S, Bjaeverskov, Denmark

[21] Appl. No.: 900,978

[22] Filed: Jun. 18, 1992

[51] Int. Cl.⁵ .............................................. A61B 17/00
[52] U.S. Cl. ...................................... 606/200; 128/859
[58] Field of Search ............... 606/200, 108; 128/899; 604/104–108

[56] References Cited

U.S. PATENT DOCUMENTS

| | | |
|---|---|---|
| 3,952,747 | 4/1976 | Kimmell, Jr. |
| 4,425,908 | 1/1984 | Simon |
| 4,619,246 | 10/1986 | Molgaard-Nielsen et al. |
| 4,643,184 | 2/1987 | Mobin-Uooin ................. 606/200 |
| 4,832,055 | 5/1989 | Palestrant ...................... 128/899 |
| 4,943,257 | 7/1990 | Saveliev et al. ................ 606/200 |
| 5,059,205 | 10/1991 | El-Nounou et al. ............ 606/200 |
| 5,147,379 | 9/1992 | Sabbaghian et al. .......... 606/200 |
| 5,201,757 | 4/1993 | Hoyn et al. .................... 606/200 |

FOREIGN PATENT DOCUMENTS

| | | |
|---|---|---|
| 0430848 | 6/1991 | European Pat. Off. |
| 2573646 | 5/1986 | France ............................ 128/899 |

Primary Examiner—Peter A. Aschenbrenner
Assistant Examiner—William Lewis
Attorney, Agent, or Firm—Richard J. Godlewski

[57] ABSTRACT

An introduction catheter set for a collapsible, self-expandable implant of the type comprising a number of spring-biased anchoring legs, e.g. a filter for entrapping thrombi or emboli into a blood vessel of a patient comprises a flexible external guide sheath and a flexible internal catheter slidably displaceable inside the guide sheath and having at its distal end a tubular end member, in which a retaining member is slidably arranged for releasably retaining the anchoring legs of the implant in defined angular positions in respect of each other. The retaining member is connected with a flexible displacement member extending throughout the internal catheter with the proximal ends of the displacement member and the internal catheter connected with a first and a second operating member, respectively. By operation of the operating members the retaining member may be displaced in the tubular end member from a retaining position, in which the anchoring legs of the implant are inside the tubular end member which protrudes from the distal end of the external sheath, to a release position, in which the retaining member protrudes from the tubular end member to release the anchoring legs of the implant.

9 Claims, 6 Drawing Sheets

INTRODUCTION CATHETER SET FOR A COLLAPSIBLE SELF-EXPANDABLE IMPLANT

The present invention relates to an introduction catheter set for a collapsible self-expandable implant into a blood vessel of a patient.

Without being limited thereto the invention is concerned in particular with the introduction of collapsible self-expandable stents or filters of the type comprising a number of diverging anchoring legs to secure correct positioning of the implant when arranged in the blood vessel.

BACKGROUND OF THE INVENTION

Filters of the above-mentioned type are used, i.a. for permanent or temporation implantation in the vena cava, in particular the inferior vena cava, to prevent thrombi or emboli from reaching the patient's lungs and causing pulmonary embolization.

Such filters are well known in the art, e.g. from U.S. Pat. Nos. 3,952,747, 4,425,908 and 4,619,246 as well as published European patent application No. 430848.

For the filter disclosed in U.S. Pat. No. 3,952,747 a relatively simple insertion instrument is described, comprising a single catheter to the distal end of which a filter carrier is connected by means of a connecting member, in which the filter legs are retained during the insertion which is performed by sliding the catheter with the filter arranged on the filter carrier directly through the blood vessels of the patient. When the carrier has been brought into position, a hydraulic pressure is applied through the catheter to act on a spring-biased piston inside the carrier whereby the spring-biased filter legs retained behind a ramp portion of the connecting member are released.

By such an instrument the risk of damage during insertion is relatively high due to the direct contact between the filter and filter carrier and the blood vessel. In addition, the filter carrier with the internal spring-biased piston is a rather complicated device which moreover entails the complication in operation that hydraulic pressure must be applied through the catheter.

For the filter disclosed in U.S. Pat. No. 4,425,908 insertion is performed by sliding a guide wire to the distal end of which the filter is connected through a catheter. To retain the filter legs is a collapsed state during displacement through the catheter the use of a shape-memory alloy for the filter is prescribed. The necessity of cooling equipment for cooling the filter to bring it to the collapsed state renders this method rather complicated.

SUMMARY OF THE INVENTION

Departing from prior art insertion techniques such as described above it is the object of the invention to provide an introduction catheter set of essentially less complicated construction and operation permitting safe introduction of implants of the type described made from relatively inexpensive materials and with an improved accuracy in the positioning of the central hub of the implant after release from the catheter set.

According to the invention an introduction catheter set is provided for introducing a collapsible, self-expandable implant, e.g. a filter for entrapping thrombi or emboli into a blood vessel of a patient, said implant being of the type comprising a number of diverging spring-biased anchoring legs to centre the implant in respect of the blood flow through said vessel, said catheter set comprising a flexible external guide sheath, a flexible internal catheter having a tubular end member at its distal end and being slidably displaceable inside said guide sheath to a position in which said tubular end member protrudes from the distal end of said sheath, and a retaining member slidably arranged in said tubular end member for releasably retaining the anchoring legs of the implant in defined angular positions in respect of each other, said retaining member being connected with a flexible displacement member extending throughout the internal catherer, the proximal ends of said displacement member and the internal catheter being connected with a first and a second operating member, respectively, by operation of which said retaining member is displaceable in respect of said tubular end member from a retaining position, in which the anchoring legs of the implant are inside said tubular end member, to a release position, in which the retaining member protrudes from the tubular end to release the anchoring legs of the implant.

In use of this catheter set the internal catheter and the flexible displacement member surrounded by it with the implant attached to the retaining member is first slidably guided through the external sheath to the desired location in a blood vessel, such as the inferior vena cava to a position in which the implant and the distal end of internal catheter protrudes from the distal end of the external sheath. In this position the ends of the anchoring legs are still retained in place inside the tubular end member of the internal catheter. By retraction of the internal catheter in respect of the displacement member, the retaining member gets clear of the tubular end member towards the position from which the anchoring legs are released and expanded as a result of their natural spring-bias.

The introduction catheter set according to the invention secures a maximum control of the implant during introduction and advancement to the intented place of implantation in a blood vessel until actual release of the anchoring legs.

Moreover, since the only rigid members of the catheter set are the tubular end member of the internal catheter and the retaining member which during introduction are axially inside the tubular end member and both members may have a short axial length, maximum flexibility is obtained compared to prior art insertion instruments.

The retention of the anchoring legs in defined angular positions in respect of each other corresponding to the angular separation of the legs in the implant itself until the moment of release effectively prevents the anchoring legs from intermeshing with one another and contributes to facilitate the implantation.

In a preferred embodiment this accurate definition of the angular positions of the anchoring legs is obtained by a design wherein said retaining member is formed as a pin-like member provided with a number of longitudinal slits for accommodation of the free ends of the anchoring legs of the implant. This design is advantageous in permitting a minimum overall diameter of the catheter set, whereby the introduction and advancement to the exact place of implantation is further facilitated.

In order to maintain control of the implantation when the implant is to be positioned in a blood vessel such as the inferior vena cava having an essentially larger diameter than the external guide sheath, additional means may be provided to position the distal end of the external guide sheath substantially centrally in the blood vessel in said retaining position.

Advantageously such positioning means may comprise a number of resilient centering legs secured to said tubular member and projecting from the distal end thereof.

BRIEF DESCRIPTION OF THE DRAWINGS

In the following the invention will be further explained with reference to the accompanying drawings in which.

Figure 1:
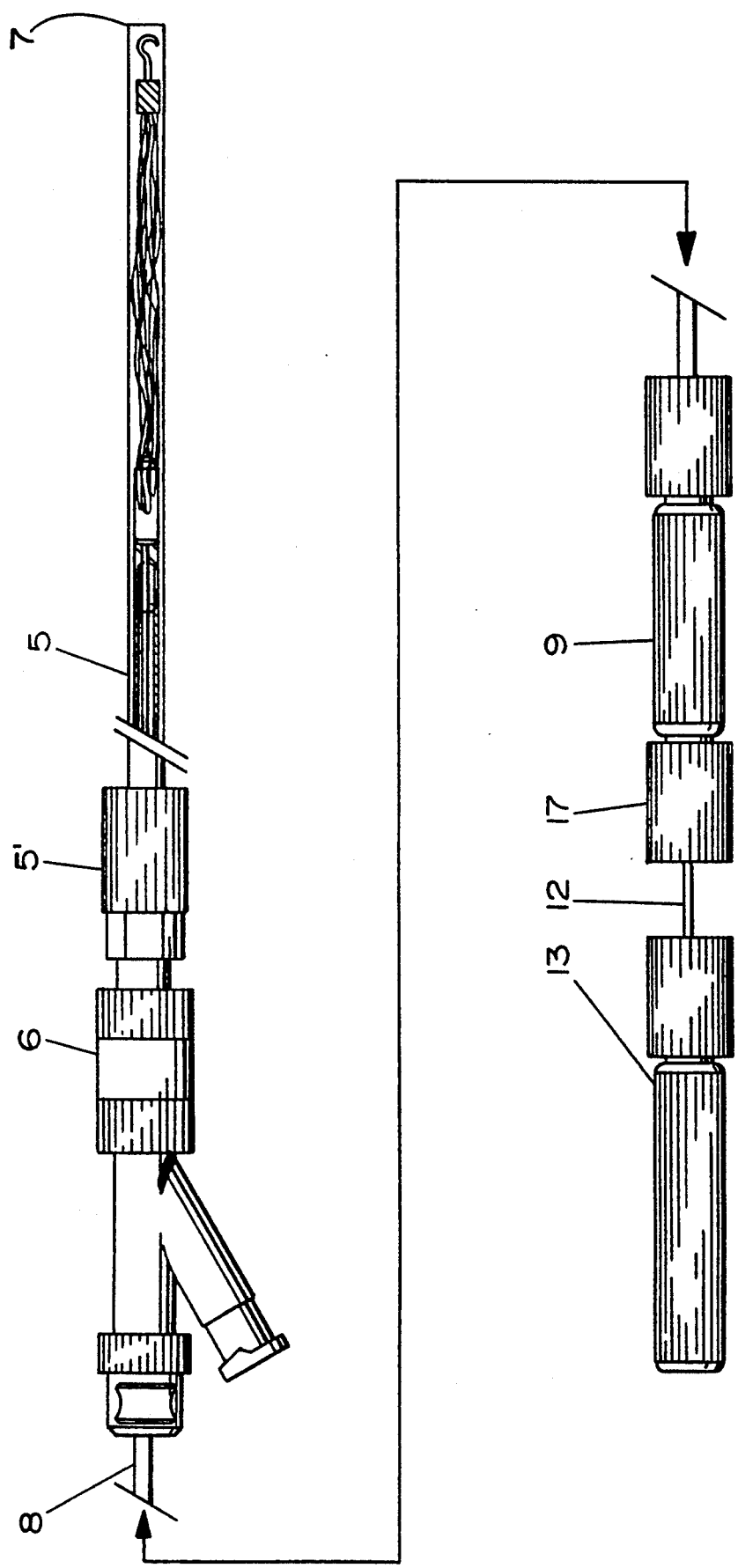
FIG. 1 is a general view of an embodiment of an introduction catheter set according to the invention intended for a vena cava filter.

The embodiment of the introduction catheter set of the invention illustrated in the drawings is intended for implantation of a collapsible vena cava filter of the kind discussed in copending U.S. patent application Ser. No. 606,588.

Figure 6:
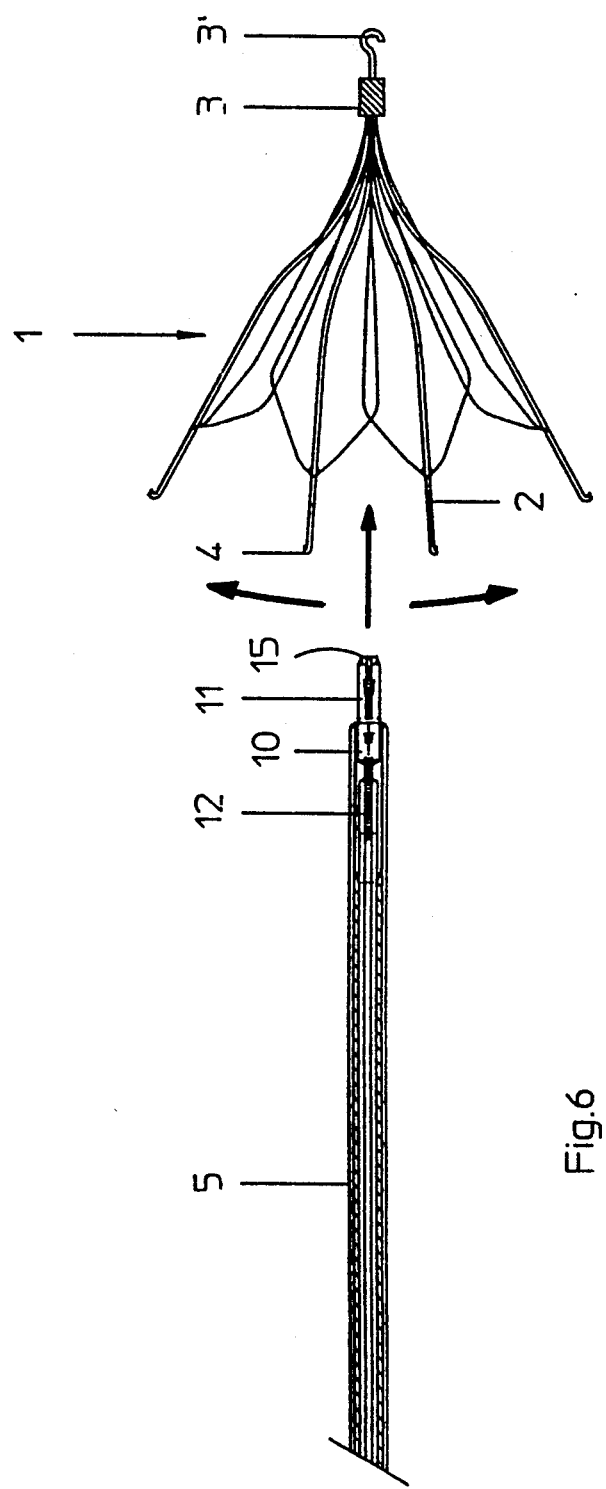

As most clearly apparent from FIG. 6, such a filter 1 comprises a number of spring-biased expandable anchoring legs 2 projecting from a common central hub member 3 and each having a bent hook 4 at the free end of the leg.

The introduction catheter set comprises a flexible external guide sheath 5 secured at its proximal end by means of a hub member 5' to a side-arm adapter 6 which may be of the so-called Tuohy-Borst type, whereas the guide sheath 5 has an open distal end 7.

A flexible internal filter catheter 8 is slidably displaceable inside the guide sheath 5 and is connected at its proximal end with an operating member 9 serving to push the filter catheter 8 through the external guide sheath 5. At its distal end the flexible internal catheter 8 is connected with a tubular end member 10.

Slidably arranded inside the tubular end member 10 is a filter retaining member 11 serving to releasably retain the anchoring legs 2 of the filter 1 inside the tubular end member 10 until the introduction catheter set has been advanced through the veins of the patient to the intended place of implantation such as the vena cava.

The retaining member 11 is connected with an elongate flexible displacement member 12 such as a wire member extending throughout the length of the internal catheter 8 and being connected at its opposite proximal end with an operating member 13.

Figure 2:
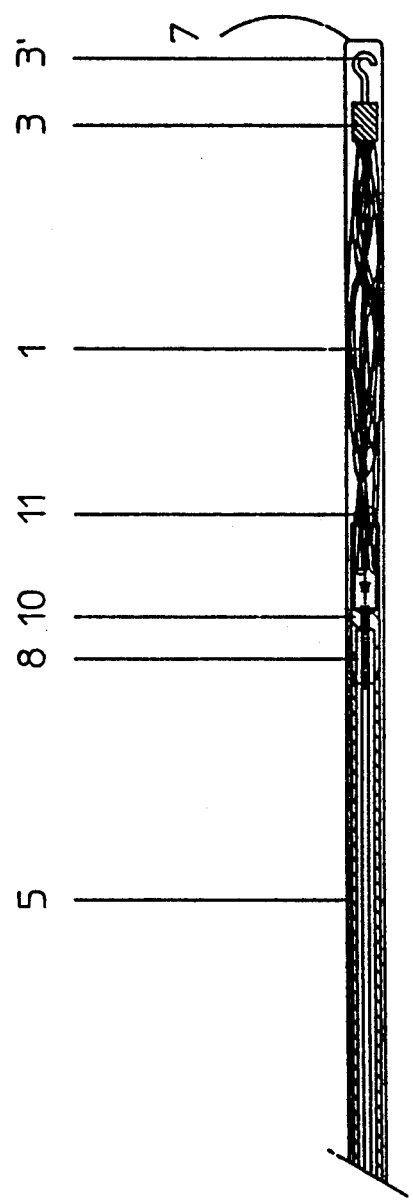
FIG. 2 is an enlarged view of the distal end view of the catheter set.

As illustrated in FIG. 2 which is an enlarged view of the distal end portion of the catheter in the introduction condition, the tubular end member 10 of the internal catheter 8 is retracted from the distal end 7 of the external guide sheath 5 over a distance permitting the filter 1 in its collapsed state to be inside the external guide sheath 5. In this condition the retaining member 11 is also retracted inside the tubular end member 10 to retain the free ends of the filter anchoring legs 2 safely inside the tubular end member 10.

This retaining position of the retaining member 11 is accomplished by safe-guarding corresponding relative positions of operating members 9 and 13 connected with the internal catheter 8 and the displacement member 12, respectively by spring bias means which may be incorporated in a manner not illustrated in operating member 9.

Moreover, in a manner known per se the adapter device 6 may have releasable arresting means for locking the internal catheter 8 in the relative position in respect of the external guide sheath 5 illustrated in FIG. 2.

Figure 3:
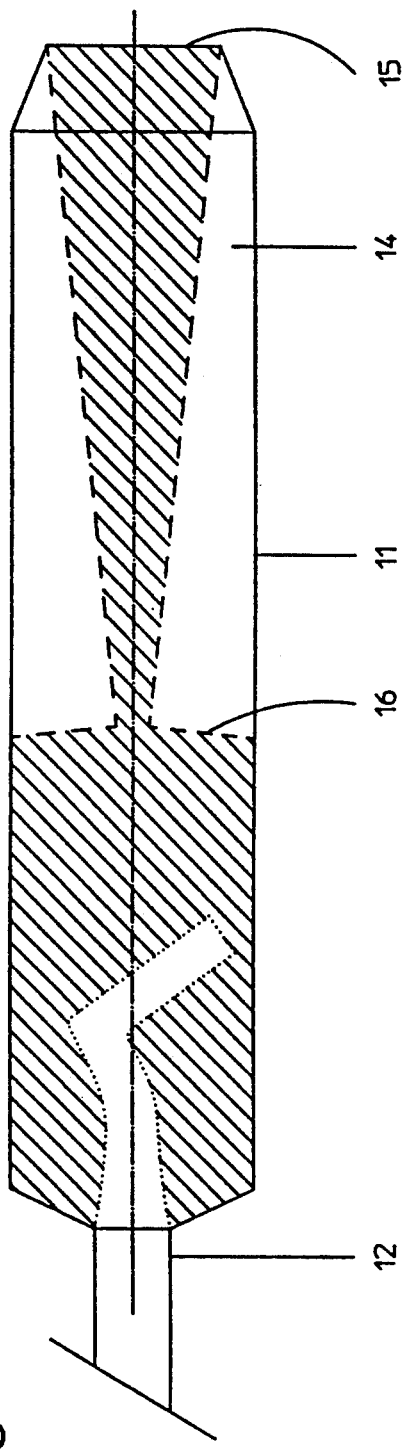
FIGS. 3 and 4 show an embodiment of the filter retaining member.
Figure 4:
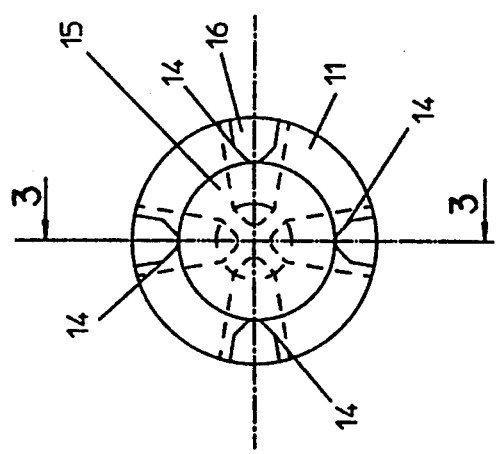

As shown in FIGS. 3 and 4, the retaining member 11 may be formed as a pin-like member which for accommodation of the free ends of the anchoring legs 2 of filter 1 is provided with a number of longitudinal slits 14 corresponding to the number of anchoring legs 2 and formed in the circumferential surface of the retaining member 11 with a uniform angular separation.

In the embodiment shown, the slits 14 extend approximately over half the length of the retaining member 11 from its distal end 15, and in order to accommodate the bent hook 4 at the free end of each anchoring leg 2 each slit has a depth increasing from the distal end 15 towards an end wall 16 at the opposite end of the slit 14.

By this design the anchoring legs 2 of a filter as shown in FIG. 6 may be fully within the slits 14 to extend inside the circumferential surface of the retaining member, which may then fit with a small clearance in respect of the tubular end member 10 of the internal catheter 8.

By displacement of the retaining member 11 in the direction out of the distal end of the tubular end member 10 by bringing operating members 9 and 13 into end-by-end contact, the retaining member 11 will be moved to a release position, in which it projects sufficiently outside the distal end of the tubular end member 10 to effect release and expansion of the anchoring legs 2 as a result of their inherent spring bias.

In actual use the introduction catheter set according to the invention may be supplied as two components, namely the external guide sheath 5 with the hub member 5' and a loading catheter system, comprising the internal catheter 8 with its operating member 9 and tubular end member 10 and arranged inside the latter, the retaining member 11 with its wire-shaped displacement member 12 and operating member 13. The side arm adapter 6 is slidably arranged on the internal catheter on the distal side of the operating member 9.

In the supply condition, the filter 1 is mounted in the tubular end member 10 by means of the retaining member 11 with the filter body projecting outside the tubular end member and covered by a peal-away sheath.

In operation the external guide sheath 5 is first advanced, following puncture of the femoral vein, e.g. by using the Seldinger technique, by use of a wire guide as know in the art to a desired place of implantation, which in this case may be in the inferior vena cava just below the renal veins.

The distal end of the internal catheter 8 with the projecting filter 1 covered by the abovementioned peal-away sheath is now advanced somewhat into the proximal end of the external guide sheath, and the peal-away sheath is removed. Thereafter, the side arm adapter 6 is displaced on the internal catheter 8 to get into connection with the hub member 5' of the external guide sheath.

The internal catheter 8 together with the wire member 12 arranged therein is now advanced in the external guide sheath 5 until the position shown in FIGS. 1 and 2, where a retrieval hook 3' at the hub member 3 of the filter 1 coincides with the distal end 7 of the external guide sheath 5.

Figure 5:
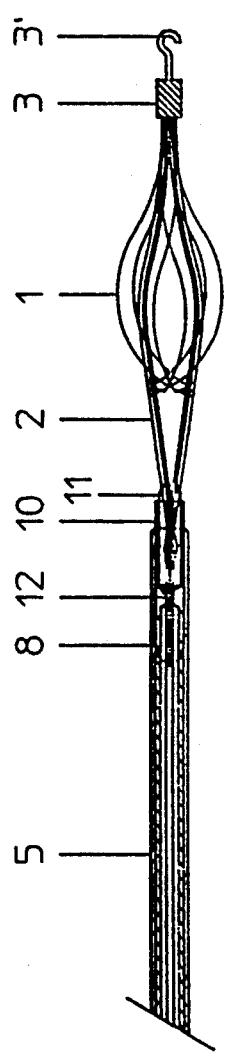
FIGS. 5 and 6 illustrate two consecutive phases of the filter release operation.

After verification of the position of implantation by means of X-ray examination, the side arm adapter 6 and with it the external guide sheath 5 is now retracted over the internal catheter 8 to the position shown in FIG. 5, in which the filter is pre-released with its body portion getting clear of the external guide sheath 5 and slightly expanded, but still with the free ends of the anchoring legs 2 retained inside the tubular end member 10 by means of the retaining member 11.

In this condition, moderate repositioning of the filter is still possible, but in the embodiment shown the filter cannot be pulled back into the external guide sheath 5 due to its shape. Proper positioning can again be verified by X-ray examination.

As shown in FIG. 5, in the pre-release position the tubular end member 10 projects with its distal end somewhat outside the distal end 7 of the external guide sheath 5. The side arm adapter 6 is secured relative to the internal catheter 8.

Whereas in the introduction stages described above, the operating members 9 and 13 have assumed mutually locked positions, e.g. by securing the operating member 9 to the wire member 12 by means of an arresting hub 17, the latter is now turned loose to permit retraction of operating member 9 towards operating member 13, whereby the retaining member 11 gets clear of the tubular end member 10 over a length slightly exceeding the length of the slits 14 in the retaining member 11, such as shown in FIG. 6.

Due to the spring bias of the anchoring legs 2, the filter 1 will now be completely released and assume the desired position of implantation with great accuracy, in which the filter is fixed in the vena cava by being anchored in respect of the vein wall by means of the bent hook ends of the anchoring legs 2.

Figure 8:
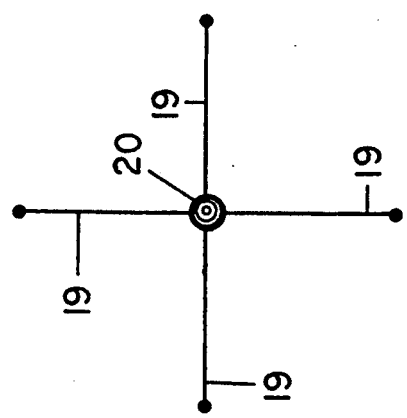
FIG. 8 shows an enlarged side view of the catheter set of FIG. 7A.
Figure 7A:
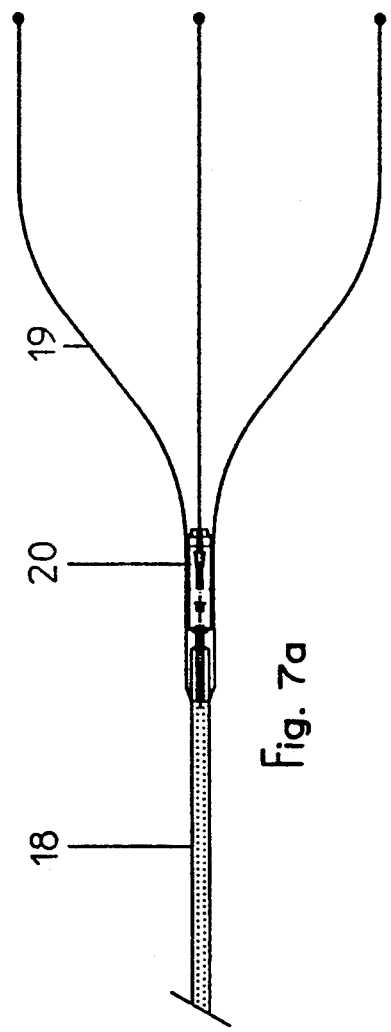
FIGS. 7A shows a modification of the catheter set with improved pre-centering function.
Figure 7B:
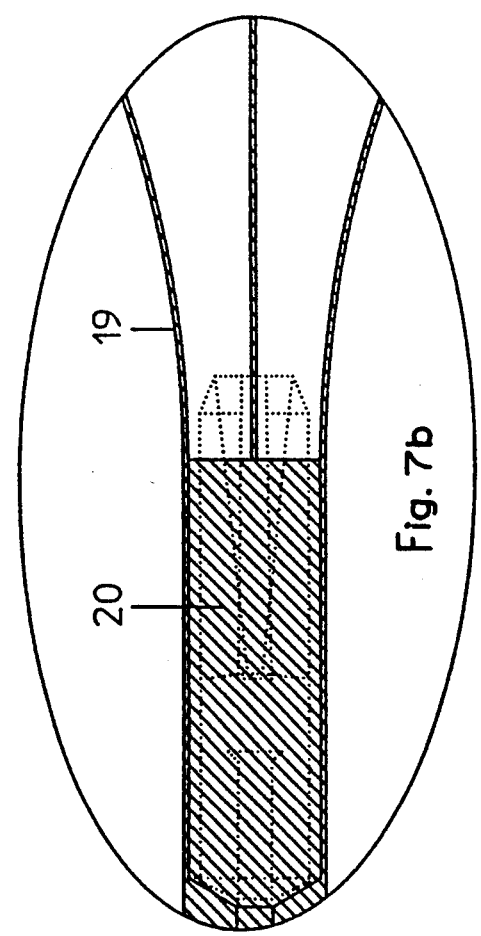
FIG. 7B shows an enlarged view of a portion of the catheter set of FIG. 7A.

FIGS. 7A, 7B and 8 show a modification of the internal catheter 8 with additional means for securing a more accurately centered positioning of the distal end of the catheter set before the release operation which may be useful in case of implantation in a blood vessel such as the vena cava, having an essentially larger diameter than the external guide sheath of the catheter set.

In the embodiment shown, the improved centering means comprises a number of spring-biased centering legs 19 secured in the tubular end member 20 of catheter 18 in such a way that the overall diameter of this member is not significantly increased, e.g. by arranging the centering legs 19 in shallow longitudinal slits in the outer circumferential surface of member 20.

In the condition of the catheter set shown in FIGS. 1 and 2, the centering legs will be inside the external guide sheath and will remain there during advancement of the catheter set to the place of implantation. In the pre-release operation as illustrated in FIG. 5, the centering legs will expand to centre the filter in the vena cava.

In order to avoid damage to the wall of the vena cava by the spring release operation of the centering legs, a small slide member having, e.g. a spherical or similar smoothly rounded surface may be provided at the free end of each centering leg 19, whereby the centering legs 19 may be safely retracted into the external guide sheath once the implantation process is completed.

The application of the filter set according to the invention is in no way limited to implantation of the specific form of a vena cava filter described in the foregoing and illustrated in the Figures byt may with the same advantages extend to other types of implantation filters or stents and similar implants to be positioned in a blood vessel and having projecting anchoring legs.

I claim:

1. An introduction catheter set for introducing a collapsible, self-expandable implant, e.g. a filter for entrapping thrombi or emboli into a blood vessel of a patient, said implant being of the type comprising a number of diverging spring-biased anchoring legs to centre the implant in respect of the blood flow through said vessel, the anchoring legs having free ends for engaging said vessel, said catheter set comprising a flexible external guide sheath, a flexible internal catheter having a tubular end member at its distal end and being slidably displaceable inside said guide sheath to a position in which said tubular end member protrudes from the distal end of said sheath, and a retaining member slidably arranged in said tubular end member for releasably retaining the free ends of the anchoring legs of the implant in defined angular positions in respect of each other, said retaining member being connected with a flexible displacement member extending throughout the internal catheter, the proximal ends of said displacement member and the internal catheter being connected with a first and a second operating member, respectively, by operation of which said retaining member is displaceable in respect of said tubular end member from a retaining position, in which the anchoring legs of the implant are inside said tubular end member, to a release position, in which the retaining member protrudes from the tubular end member to release the anchoring legs of the implant.

2. A catheter set as claimed in claim 1, wherein said retaining member is formed as a pin-like member provided with a number of longitudinal slits for accommodation of the free ends of the anchoring legs of the implant.

3. A catheter set as claimed in claim 2, wherein said longitudinal slits extend through part of the length of the retaining member from the distal end thereof and each has a depth increasing from said distal end to accommodate a bent hook at the end of the respective anchoring leg.

4. A catheter set as claimed in claim 1, wherein spring bias means is provided to bias said first and second operating members into relative positions corresponding to the retaining position of said retaining member.

5. A catheter set as claimed in claim 1, wherein said second operating member is a tubular member co-axially surrounding an exposed part of the flexible displacement member protruding from the proximal end of the internal catheter and being provided with arresting means for arresting the second operating member in respect of the displacement member.

6. An introduction catheter set as claimed in claim 1, wherein means are provided to position the distal end of the external guide sheath substantially centrally in the blood vessel in said retaining position.

7. An introduction catheter set as claimed in claim 6, wherein said positioning means comprises a number of resilient centering legs secured to said tubular member and projecting from the distal end thereof.

8. An introduction catheter set as claimed in claim 7, wherein said centering legs are retained and secured in longitudinal slits formed in the external surface of the tubular member.

9. An introduction catheter set as claimed in claim 7, wherein friction reducing slide members are provided at the free ends of the positioning legs.

* * * * *